United States Patent
Huang et al.

(10) Patent No.: US 10,327,631 B2
(45) Date of Patent: Jun. 25, 2019

(54) POST-PROCESSING REDUCTION OF FIXED PATTERN ARTIFACTS AND TRIGGER JITTER IN SWEPT-SOURCE OPTICAL COHERENCE TOMOGRAPHY

(71) Applicants: David Huang, Portland, OR (US); Gangjun Liu, Portland, OR (US)

(72) Inventors: David Huang, Portland, OR (US); Gangjun Liu, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 95 days.

(21) Appl. No.: 14/996,134

(22) Filed: Jan. 14, 2016

(65) Prior Publication Data

US 2016/0206195 A1    Jul. 21, 2016

Related U.S. Application Data

(60) Provisional application No. 62/104,230, filed on Jan. 16, 2015.

(51) Int. Cl.
| | |
|---|---|
| *G01B 9/02* | (2006.01) |
| *A61B 3/10* | (2006.01) |
| *A61B 3/00* | (2006.01) |
| *A61B 3/12* | (2006.01) |

(52) U.S. Cl.
CPC ............ *A61B 3/102* (2013.01); *A61B 3/0025* (2013.01); *A61B 3/1233* (2013.01); *G01B 9/02004* (2013.01); *G01B 9/0207* (2013.01); *G01B 9/02091* (2013.01)

(58) Field of Classification Search
CPC ..... A61B 3/102; A61B 3/0025; A61B 3/1233; G01B 9/02004; G01B 9/0207; G01B 9/02072; G01B 9/02074; G01B 9/02075; G01B 9/02091
USPC .................................................. 356/479, 497
See application file for complete search history.

(56) References Cited

U.S. PATENT DOCUMENTS

| | | | | |
|---|---|---|---|---|
| 2010/0091145 A1* | 4/2010 | Iseri | ........................ | H04N 5/365 348/243 |
| 2017/0074640 A1* | 3/2017 | Cable | ................. | G01B 9/02083 |

OTHER PUBLICATIONS

Phase-stabilized optical frequency domain imaging at 1-μm for the measurement of blood flow in the human choroid, Braaf et al, Oct. 2011, vol. 19 No. 22, Optics Express.*

(Continued)

*Primary Examiner* — Tarifur R Chowdhury
*Assistant Examiner* — Jonathon Cook
(74) *Attorney, Agent, or Firm* — Schwabe, Williamson & Wyatt, P.C.

(57) ABSTRACT

Disclosed herein are methods and systems for aligning swept-source optical coherence tomography (SS-OCT) spectral interferograms to a reference spectral interferogram based on signal information (e.g., amplitude or phase) at a fixed-pattern noise location to reduce residual fixed-pattern noise and improve the phase stability of SS-OCT systems.

21 Claims, 11 Drawing Sheets

(56) References Cited

OTHER PUBLICATIONS

Three-dimensional and high-speed swept-source optical coherence tomography for in vivo investigation of human anterior eye segments, Yasuno et al, optics express, vol. 13, Issue 26, pp. 10652-10664 (2005).*

Ultra high-speed swept source OCT imaging of the anterior segment of human eye at 200 kHz with adjustable imaging range, Gora et al, Optics Express vol. 17, Issue 17, pp. 14880-14894 (2009).*

Removing the depth-degeneracy in optical frequency domain imaging with frequency shifting, Yun et al Optics express, vol. 12, Issue 20, pp. 4822-4828 (2004).*

* cited by examiner

POST-PROCESSING REDUCTION OF FIXED PATTERN ARTIFACTS AND TRIGGER JITTER IN SWEPT-SOURCE OPTICAL COHERENCE TOMOGRAPHY

ACKNOWLEDGMENT OF GOVERNMENT SUPPORT

This invention was made with United States government support under the terms of grant number R01EY023285 awarded by the National Institutes of Health. The United States government has certain rights in this invention.

FIELD

The present disclosure relates to the field of optical coherence tomography (OCT), and, more specifically, to systems and methods for minimizing pattern artifacts and reducing trigger jitter in swept-source OCT (SS-OCT).

BACKGROUND

Swept-source optical coherence tomography (SS-OCT) is able to achieve very high scan speeds and is less susceptible to spectral interferogram fringe washout than spectral domain OCT (SD-OCT) [1, 2]. Therefore, it has advantages for both structural and Doppler OCT imaging. However, in some SS-OCT systems, there is uncertainty in trigger timing so that the starting point of the spectral interferogram acquisition changes from cycle to cycle in wavenumber (k) space. For phase-sensitive OCT measurements such as Doppler OCT, this jitter will reduce the precision of phase measurements. In addition, trigger jitter reduces the effectiveness of subtractive removal of fixed-pattern noise artifacts (lines at fixed depths in OCT B-scans) arising from unintended internal reflections from fiber tips and sample/reference arm optics [3].

A few numerical methods have been proposed to improve the phase stability of SS-OCT systems [3-7]. However, these methods typically cannot remove the residual fixed-pattern noise. In one example approach, a method to eliminate residual fixed-pattern noise and improve the phase stability may be performed by resampling the wavenumber using a simultaneously recorded calibration signal from an interferometer [8]. However, such an approach requires another reference calibration signal as well as another digitizer channel. Thus, the system complexity and cost will be greatly increased. In another example approach, a narrow band fiber Bragg grating (FBG) may be used to produce a reference dip in acquired spectral interferograms so that the spectral interferograms can be shifted accordingly [9]. However, introduction of a FBG in such an approach may induce additional power loss and increase system cost.

SUMMARY

The present disclosure is directed to methods and systems for aligning spectral positions of swept-source optical coherence tomography (SS-OCT) spectral interferograms, e.g., interferograms affected by trigger jitter, to a reference spectral interferogram based on information (e.g., amplitude or phase) at a fixed-pattern noise location to reduce residual fixed-pattern noise and improve the phase stability of SS-OCT systems.

In one example approach, a computer-implemented method of aligning swept-source SS-OCT interferograms comprises calculating a relative wavenumber shift between an SS-OCT interferogram and a reference SS-OCT interferogram based on signal information of the interferogram and the reference interferogram at a fixed-pattern noise location; and aligning the interferogram to the reference interferogram based on the calculated relative wavenumber shift.

In embodiments described herein, internal reflections in an SS-OCT system that cause residual fixed-pattern noise may be used in post-processing as a reference to align the interferograms in k-space (wavenumber space). In contrast to previous approaches for phase-stabilization and fixed-pattern removal for SS-OCT, embodiments described herein may be used to produce substantially fixed-pattern noise free and phase stable OCT images during post-processing of acquired SS-OCT data without additional hardware or hardware modifications of an existing OCT system.

The above Background and Summary sections are provided to introduce a selection of concepts in a simplified form that are further described below in the Detailed Description. The Background and Summary are not intended to identify key features or essential features of the disclosed subject matter, nor are they intended to be used to limit the scope of the disclosed subject matter. Furthermore, the disclosed subject matter is not limited to implementations that solve any or all disadvantages noted in any part of this disclosure. Additionally, issues identified throughout this disclosure are not necessarily admitted to be well known and are recognized by the inventors of the present application.

DETAILED DESCRIPTION

The following detailed description is directed methods and systems for aligning spectral positions of swept-source optical coherence tomography (SS-OCT) spectral interferograms to a reference spectral interferogram based on signal information (e.g., intensity/amplitude or phase) at a fixed-pattern noise location to reduce residual fixed-pattern noise and increase the phase stability of SS-OCT systems. In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense. Various operations may be described as multiple discrete operations in turn, in a manner that may be helpful in understanding embodiments; however, the order of description should not be construed to imply that these operations are order dependent. Additionally, in some examples, one or more of the herein-described operations may be omitted without departing from the scope of this disclosure.

Figure 1:
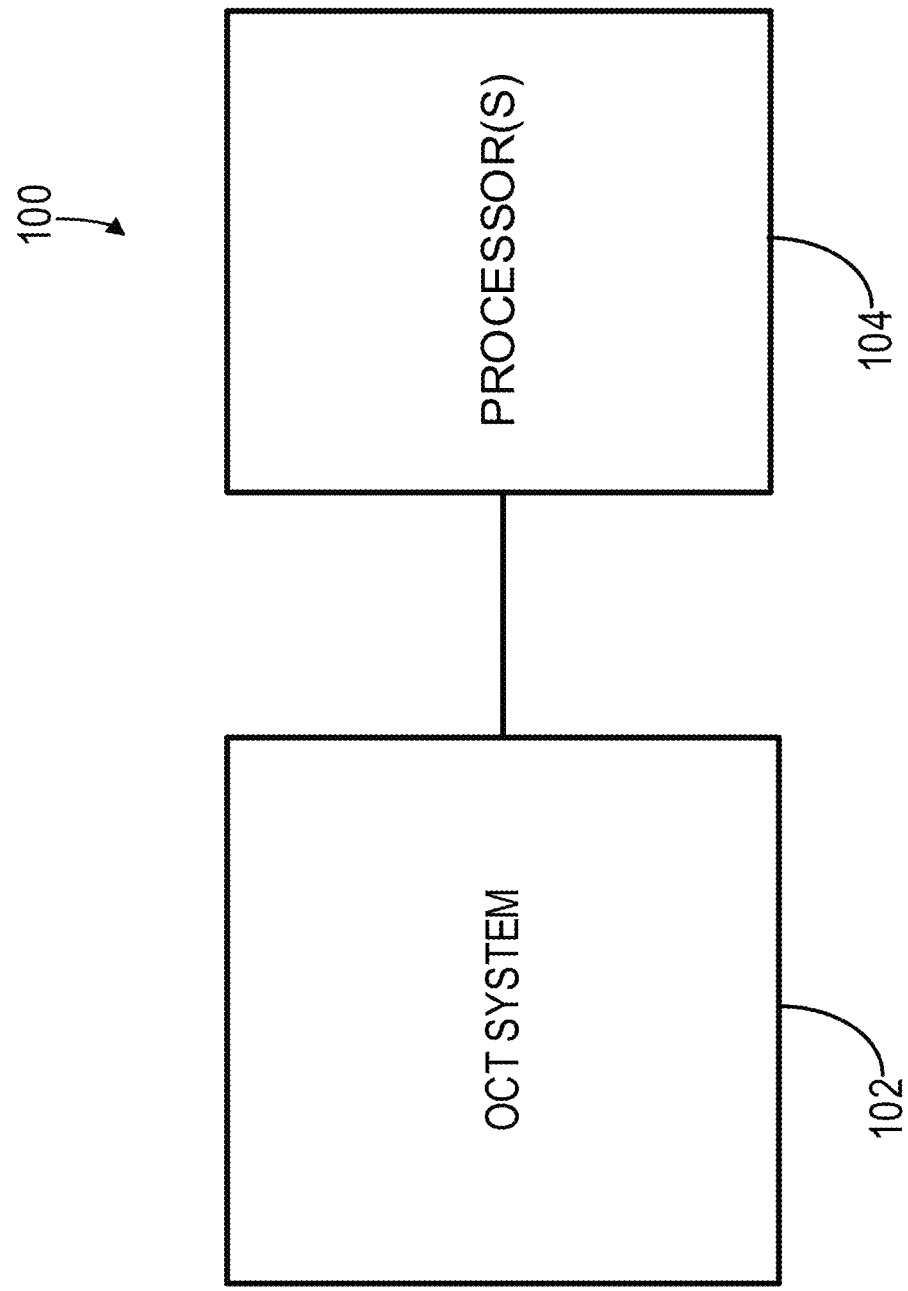
FIG. 1 schematically shows an example system for aligning swept-source optical coherence tomography (SS-OCT) spectral interferograms in accordance with the disclosure.

FIG. 1 schematically shows an example system 100 for aligning SS-OCT interferograms in accordance with various embodiments. System 100 comprises an OCT system 102 configured to acquire an OCT image comprising OCT interferograms and one or more processors or computing systems 104 that are configured to implement the various processing routines described herein. OCT system 100 may comprise a swept-source OCT (SS-OCT) system, e.g., as shown schematically in FIG. 2 described below. In a swept-source OCT implementation of Fourier-domain OCT, the light source is a laser that is very rapidly and repetitively tuned across a wide spectrum and the spectral interferograms are captured sequentially.

In various embodiments, an OCT system may be adapted to allow an operator to perform various tasks. For example, an OCT system may be adapted to allow an operator to configure and/or launch various ones of the herein described methods. In some embodiments, an OCT system may be adapted to generate, or cause to be generated, reports of various information including, for example, reports of the results of scans run on a sample.

In embodiments of OCT systems comprising a display device, data and/or other information may be displayed for an operator. In embodiments, a display device may be adapted to receive an input (e.g., by a touch screen, actuation of an icon, manipulation of an input device such as a joystick or knob, etc.) and the input may, in some cases, be communicated (actively and/or passively) to one or more processors. In various embodiments, data and/or information may be displayed, and an operator may input information in response thereto.

Figure 2:
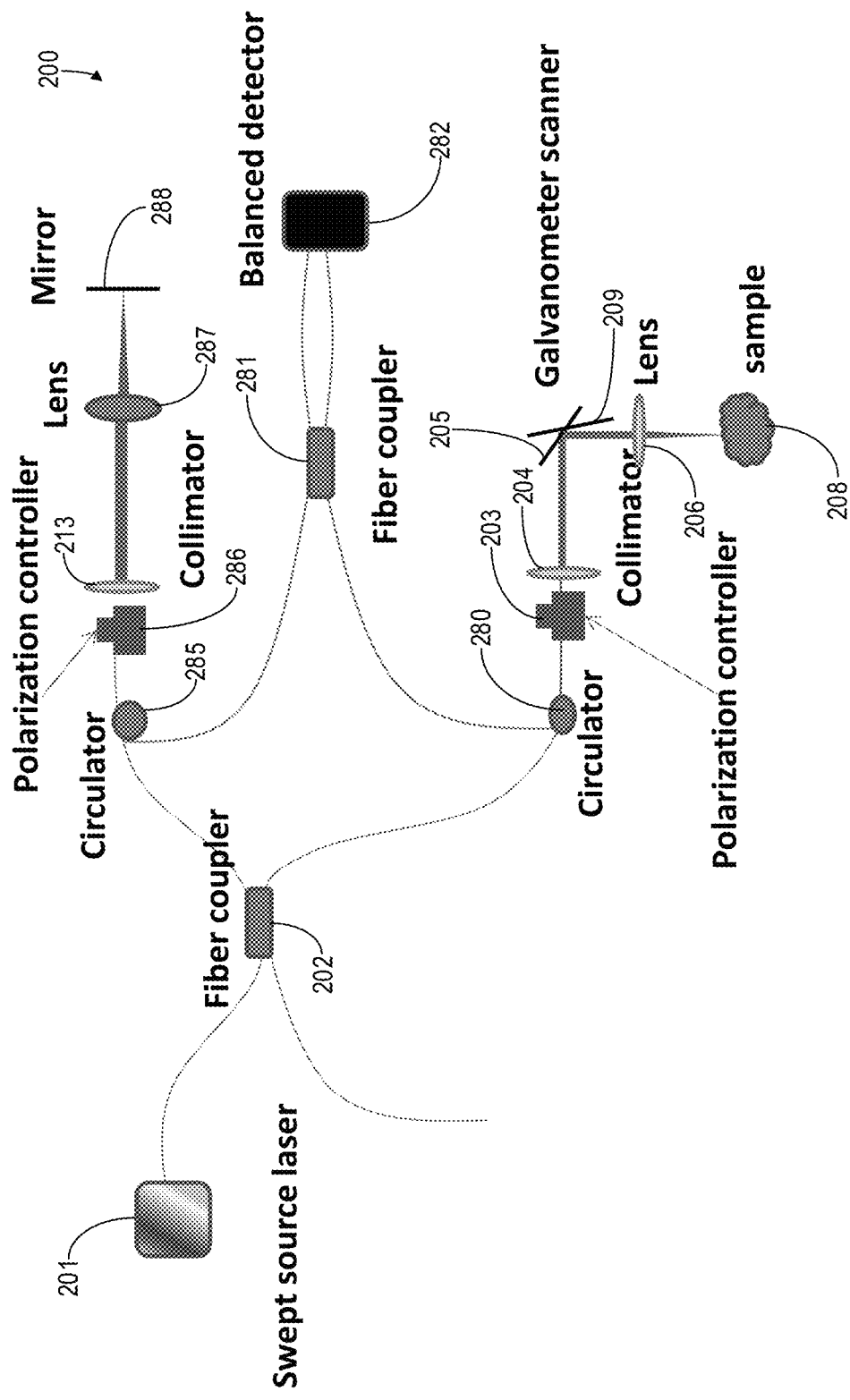
FIG. 2 schematically shows an example SS-OCT system in accordance with the disclosure.

FIG. 2 schematically illustrates an example swept-source Fourier-domain OCT system 200 for collecting OCT image information. For example, a high-speed swept-source OCT system as described in Potsaid et al., Opt. Express 18(19), 20029-20048 (2010), which is hereby incorporated by reference, can used to implement the herein described methods. Swept-source OCT system 200 comprises a tunable laser 201. For example, tunable laser 201 (e.g., a tunable laser from Axsun Technologies, Inc, Billerica, Mass., USA) may have a wavelength of 1050 nm with 100 nm tuning range, a tuning cycle with a repetition rate of 100 kHz and a duty cycle of 50%. As another example, the tunable laser 201 may have a wavelength of 1310 nm with a 100 nm tuning range, a tuning cycle with a repetition rate of 50 kHz and a duty cycle of 50%. Light from swept source 201 can be coupled into a two by two fiber coupler 202 through a single mode optical fiber. One portion of the light (e.g., 90%) can proceed to the sample arm and the other portion of the light (e.g., 10%) can proceed to the reference arm.

In the sample arm, a sample arm polarization control unit 203 can be used to adjust light polarization state. The light from the fiber coupler 202 can pass through the polarization controller 203 to be collimated by a sample arm collimating lens 204 and reflected by two axial galvanometer mirror scanners (205, 209). Lens 206 can relay the probe beam reflected by the galvanometer mirror scanners (205, 209) into a sample 208. Light from fiber coupler 202 can also pass through a reference arm polarization controller 286 to be collimated by a reference arm collimating lens 213. Lens 287 can focus the beam onto a reference mirror 288 and the light reflected back from mirror can enter the collimator 213.

Via circulators 280 and 285, light scattered back from the sample and reflected back from the reference arm can interfere at fiber coupler 281 to be detected by a balanced detector 282 (e.g., a balanced receiver manufactured by Thorlabs, Inc, Newton, N.J., USA). The signals detected by detector 282 can be sampled by an analog digital conversion unit (e.g., a high speed digitizer manufactured by Innovative Integration, Inc.) and transferred into a computer or other processor for processing.

As remarked above, previous approaches proposed to improve the phase stability of SS-OCT systems have either not been effective at removing the residual fixed-pattern noise and/or require additional hardware or hardware modifications and/or processing routines that increase system complexity, increase cost, and/or increase power consumption in an SS-OCT system.

Accordingly, in embodiments described herein, internal reflections in an SS-OCT system that cause residual fixed-pattern noise may be used in post-processing as a reference to align the interferograms in k-space (wavenumber space). In contrast to previous approaches for phase-stabilization and fixed-pattern removal for SS-OCT, embodiments described herein may be used to produce substantially fixed-pattern noise free and phase stable OCT images during post-processing of acquired SS-OCT data without additional hardware or hardware modifications of an existing OCT system. Additionally, embodiments described herein may be implemented without substantially increasing power consumption during processing of SS-OCT data to reduce residual fixed-pattern noise.

In embodiments described herein, instead of using an averaged background interferogram as the reference interferogram, a single interferogram, e.g., a single background interferogram, may be used as a reference interferogram $A_r(n)$, where n is the index of the sampling point for the interferogram and n is linear with wavenumber. Assuming the interferogram of interest $A_s(n)$ is wavenumber shifted relative to $A_r(n)$ and the inverse Fourier transform of $A_r(n)$ is $I_r(z)$, the following equations hold:

$$A_s(n) = A_r(n - m_s), \qquad (1)$$

$$F^{-1}[A_r(n)] = I_r(z), \qquad (2)$$

-continued $$F^{-1}[A_s(n)] = I_s(z) = e^{-i\frac{2\pi}{N}m_s z} I_r(z), \quad (3)$$

$$I_{sr}(z) = I_s(z) - I_r(z) = I_r(z)\S(m_s, z). \quad (4)$$

Figure 4:
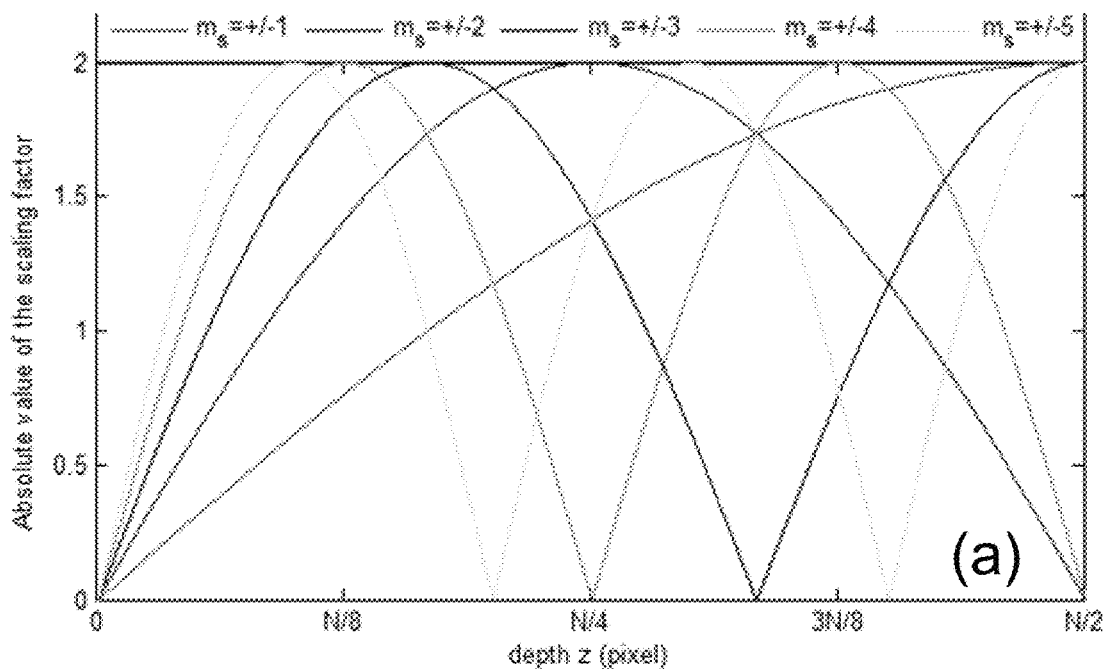
FIG. 4 shows an example graph of a relationship between a scaling factor, depth, and wavenumber shift and an example graph showing values for real and imaginary parts of example scaling factors at a particular depth.
Figure 4:
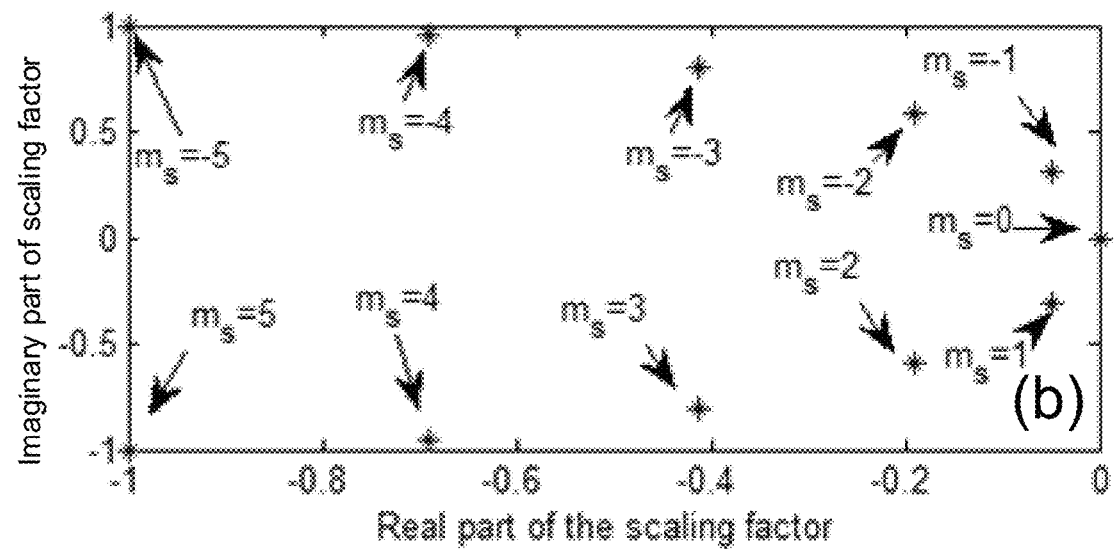

In the above equations, $m_s$ is the relative wavenumber shift (relative k-shift) in the sampling points between the interferogram of interest $A_s$ and reference interferogram $A_r$, $F^{-1}$ [ ] represents an inverse Fourier transform, $\S(m_s, z)$ is a scaling factor defined by $$\S(m_s, z) = \left(e^{-i\frac{2\pi}{N}m_s z} - 1\right),$$

and N is the number of wavenumber samples in the interferogram. If $m_s=0$, namely that there is no relative k-shift between the two interferograms, the scaling factor $\S(m_s, z)=0$ and $I_{rs}(z)=0$. For the cases where $m_s \neq 0$, the amplitude scaling factor $|\S(m_s, z)|$ represents the ratio between $|I_{sr}(z)|$ and $|I_r(z)|$. The amplitude scaling factor is a function of both $m_s$ and z. FIG. 4, panel a shows the relationship between the amplitude scaling factor $|\S(m_s, z)|$, z, and $m_s$. For certain $m_s$, $|\S(m_s, z)|$ is depth dependent. At certain depths, $|\S(m_s, z)|$ is $m_s$ dependent. FIG. 4, panel b shows the values for real and imaginary parts of the scaling factor $\S(m_s, z)$ at a depth of z=0.05N. At this depth, the value of $m_s$ may be obtained from the value of scaling factor.

For the case of residual fixed-pattern noise at depth $z_f$, the value of $m_s$ can be calculated from the phases, amplitudes or complex values of $I_r(z_f)$, $I_s(z_f)$ and $I_{sr}(z_f)$. This can be seen from FIG. 4, panel b. Different k-shifts ($m_s$) may result in different scaling factors and the value of $m_s$ can be obtained from values (such as the phase, the imaginary part or the complex value) of the scaling factor. Various approaches may be used to calculate the relative wavenumber shift $m_s$. As a first example approach (method A), $m_s$ may be calculated from the complex values for $I_s$ and $I_r$ at the fixed-pattern noise location and from Equation 3 according to the following Equation 5:

$$m_s = \text{angle}[I_s(z_f)/I_r(z_f)] * N/(2\pi z_f) \quad (5)$$

In Equation 5, angle[ ] represents the phase extraction function. In some examples, phase unwrapping may be used to calculate $m_s$ using Equation 5. In a second example approach (method B), a relative k-shift may be introduced in $A_s(n)$, and a search may be performed to identify the k-shift that minimizes $|\S|$ or $|I_{sr}(z_f)|$. Based on Equation 4, the scaling factor $|\S|$ and $|I_{sr}(z_f)|$ may be zero if there is no relative shift. The shift that minimizes $|\S|$ or $|I_{sr}(z_f)|$ may be taken as the value for $m_s$. Method A uses only the phase information and the calculation of $m_s$ is straightforward according to Equation 5. Method B uses only the amplitude/intensity information and uses a search scheme to calculate $m_s$.

Figure 3:
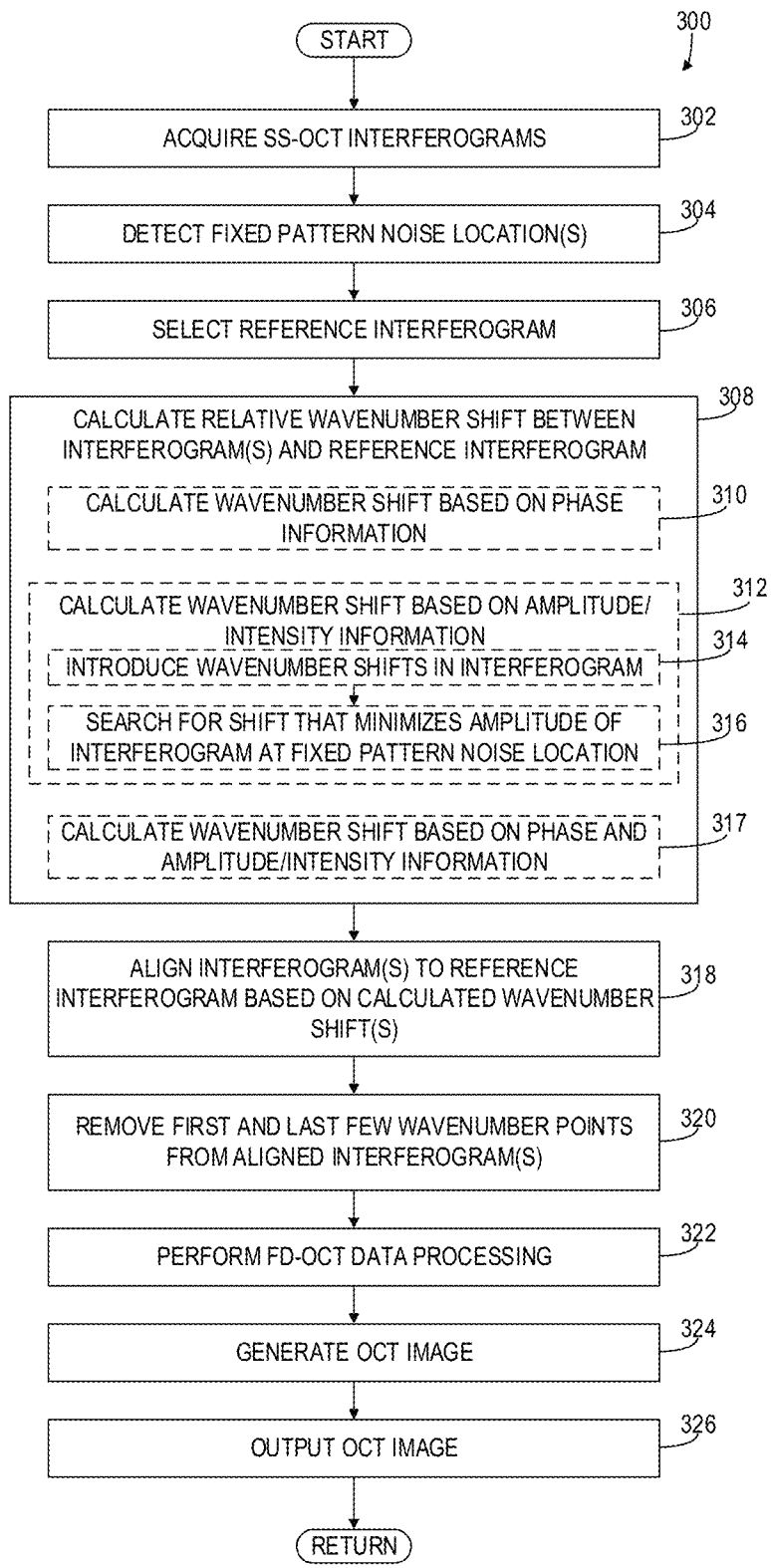
FIG. 3 shows an example method for aligning SS-OCT spectral interferograms in accordance with the disclosure.

FIG. 3 shows an example method 300 for aligning SS-OCT interferograms in accordance with various embodiments. Method 300 may be implemented by a system, such as system 100 described above, that includes an SS-OCT system and one or more processors or computing systems, such as computing device 800 described below. For example, one or more operations described herein may be implemented by one or more processors having physical circuitry programmed to perform the operations. In embodiments, one or more steps of method 300 may be automatically performed by one or more processors or computing devices. Further, various acts illustrated in FIG. 3 may be performed in the sequence illustrated, in other sequences, in parallel, or in some cases omitted. Method 300 may be used to align interferograms affected by trigger jitter to a reference interferogram based on information (e.g., amplitude/intensity or phase) at a fixed-pattern noise location to eliminate or substantially reduce residual fixed-pattern noise and increase the phase stability of SS-OCT systems.

At 302, method 300 includes acquiring SS-OCT interferograms. For example, OCT data including a plurality of interferograms may be acquired from an SS-OCT system, e.g., the SS-OCT system shown in FIG. 2. In embodiments, the OCT data may be received by a computing device from an OCT scanning system via a network or from a storage medium coupled to or in communication with the computing device. The OCT data may be obtained from any suitable swept-source Fourier-domain OCT scanning device.

At 304, method 300 may include detecting one or more fixed pattern noise locations in the OCT data. In some examples, a thresholding algorithm may be used to identify signal peaks in one or more interferograms to detect fixed pattern noise locations. For example, in response to interferogram intensities at a location (e.g., at a particular depth or range of depths) greater than a threshold, that location may be identified as a fixed pattern noise location.

Once one or more fixed pattern noise locations are detected in the OCT data, a particular fixed pattern noise location may be selected for calculating relative wavenumber shifts as described below. Different fixed-pattern noise locations in the OCT data may be generated by the same amount of k-shift. Thus, in some examples, any fixed-pattern noise location may be used to find the k-shift and the k-shift from different fixed-pattern noise locations may be at least approximately the same. However, in some examples a fixed pattern noise location around a zero frequency or close to a maximum imaging range of the SS-OCT system used to acquire the interferograms may be selected for calculating relative wavenumber shifts so that the sample image is not overlapped with the reference residual fixed-pattern noise. However, if the system does not have residual fixed-pattern noise and one still desires to improve the system phase stability, an artificial fixed-pattern noise artifact may be generated. Thus, in some examples, the OCT data may not include any fixed pattern noise locations and an artificial fixed-pattern noise artifact may be introduced at a location prior to aligning the interferograms as described below. This could be achieved by adding a thin glass plate in the reference arm or using a calibration mirror with an OCT signal that appears in the imaging range of the system, for example.

At 306, method 300 may include selecting a reference interferogram. In some examples, an interferogram may be randomly selected from a plurality of interferograms included in the OCT data and the randomly selected interferogram may be used as a reference interferogram. As an example, the reference interferogram may comprise a single background interferogram.

At 308, method 300 includes calculating a relative wavenumber shift (relative k-shift) between one or more interferograms included in the OCT data and the reference interferogram. In some examples, a relative wavenumber shift may be calculated for each interferogram in the OCT data. The calculation of a relative wavenumber shift between an SS-OCT interferogram and a reference SS-OCT interferogram may be based on signal information of the interferogram and the reference interferogram at the selected fixed-pattern noise location. For example, calculating the relative wavenumber shift between the interferogram and the reference interferogram may comprise calculating the relative wavenumber shift from the phases, amplitudes or complex values of $I_r(z_f)$, $I_s(z_f)$ and $I_{sr}(z_f)$, where $z_f$ is a depth of the residual fixed-pattern noise location, $I_r(z_f)$ is an inverse Fourier transform of the reference interferogram at depth $z_f$, $I_s(z_f)$ is an inverse Fourier transform of the interferogram of interest at depth $z_f$, and $I_{sr}(z_f) = I_s(z_f) - I_r(z_f)$.

As remarked above, the relative wavenumber shift may be calculated in a variety of ways. In one example (corresponding to method A described above) at 310, method 300 may include calculating the relative wavenumber shift using only phase information at the residual fixed pattern noise location. For example, the relative wavenumber shift ($m_s$) between the interferogram and the reference interferogram may be calculated according to the equation $m_s = \text{angle}[I_s(z_f)]/I_r(z_f)]*N/(2\pi z_f)$, where $z_f$ is a depth of the residual fixed-pattern noise location, N is the number of wavenumber samples in the interferogram, $I_r(z_f)$ is an inverse Fourier transform of the reference interferogram at depth $z_f$, $I_s(z_f)$ is an inverse Fourier transform of the interferogram of interest at depth $z_f$, and angle[ ] is a phase extraction function.

As another example (corresponding to method B described above), at 312, method 300 may include calculating the wavenumber shift based on amplitude or intensity information. For example, calculating the relative wavenumber shift between the interferogram and the reference interferogram may comprise, at 314, introducing wavenumber shifts (k-shifts) in the interferogram and, at 316, searching (via a search scheme) for a k-shift that minimizes an amplitude of the interferogram at the fixed pattern noise location. In this example, the relative wavenumber shift comprises a k-shift that minimizes the amplitude of the interferogram at the fixed pattern noise location. The amplitude of the interferogram at the fixed pattern noise location used for the k-shift search may be calculated in any suitable way. In one example, the amplitude of the interferogram at the fixed pattern noise location may comprise a sum over a predetermined number of pixels, e.g., three pixels, centered at a peak of fixed pattern noise at the fixed pattern noise location.

As yet another example, at 317, method 300 may include calculating the wavenumber shift based on both amplitude/intensity and phase information. For example, the wavenumber shift may be calculated using both methods A and B described above.

At 318, method 300 includes aligning the interferogram(s) to the reference interferogram based on the calculated wavenumber shift(s). In some examples, aligning an interferogram to the reference interferogram based on the calculated relative wavenumber shift may comprise multiplying an inverse Fourier transform of the reference interferogram by a scaling factor, wherein the scaling factor is calculated based on the calculated relative wavenumber shift for the interferogram. For example, the scaling factor may be calculated according to the equation $$e^{-i\frac{2\pi}{N}m_s z} - 1,$$

where $m_s$ is the relative wavenumber shift, N is the number of wavenumber samples in the interferogram, and z is a depth of the fixed-pattern noise location.

After the alignment of the interferograms, the values for the first or last few wavenumber sample points in some interferograms may be missing. Thus, in some examples, at 320, method 300 may include removing the first and last few wavenumber points from aligned interferograms. For example, a predetermined number of wavenumber points may be removed from the head and tail ends of the aligned interferograms. Alternatively, the missing values in the aligned interferograms may be obtained by interpolation, e.g., by simply adding zeros or using the adjacent data values.

At 322, method 300 may include performing Fourier domain OCT (FD-OCT) data processing. For example, one or more of background subtraction, Gaussian window spectral shaping, numerical dispersion compensation, and/or inverse Fourier transforms may be performed on each aligned interferogram. Additionally, other processing operations may be performed prior to or following alignment of the interferograms with the reference interferogram. For example, the OCT spectrum may be split to reduce predominant bulk-motion noise in the axial dimension where OCT resolution is very high, e.g., using a split-spectrum amplitude-decorrelation angiography (SSADA) approach as described in U.S. application Ser. No. 14/348,547, which is hereby incorporated by reference in its entirety.

At 324, method 300 may include generating an OCT image based on the aligned interferograms. For example, a structural OCT image and/or a Doppler OCT image may be generated. At 326, method 300 may include outputting the generated OCT image to a display device and/or storage medium.

EXAMPLE

The example discussed below illustrates methods and systems for aligning swept-source optical coherence tomography (SS-OCT) interferograms to a reference interferogram based on signal information at a fixed-pattern noise location, in accordance with various embodiments. Embodiments may vary as to the methods of obtaining OCT image data, performing OCT data processing, and aligning interferograms of the OCT data. The example discussed below is for illustrative purposes and is not intended to be limiting.

In this example, a SS-OCT retinal imaging system was used for demonstration. The system used a swept source laser (Axsun 1050, AXSUN Technologies Inc., Billerica, Mass.) with a central wavelength of 1050 nm and an A-line rate of 100 kHz. The signal from the balanced detector was sampled with a high speed 400 MHz digitizer (Innovative integration X5-400M) using the built-in trigger and clock signals from the Axsun laser. The system had an axial resolution of approximately 7 μm in air and lateral resolution of 23 μm. For each interferogram, there were 1400 useful sample points. Due to unintended reflections from fiber tips, sample/reference arm optics, and an unstable A-line trigger, there were a few fixed-pattern noise locations in the OCT B-scan images. One prominent fixed-pattern noise was around the zero depth position.

Figure 5:
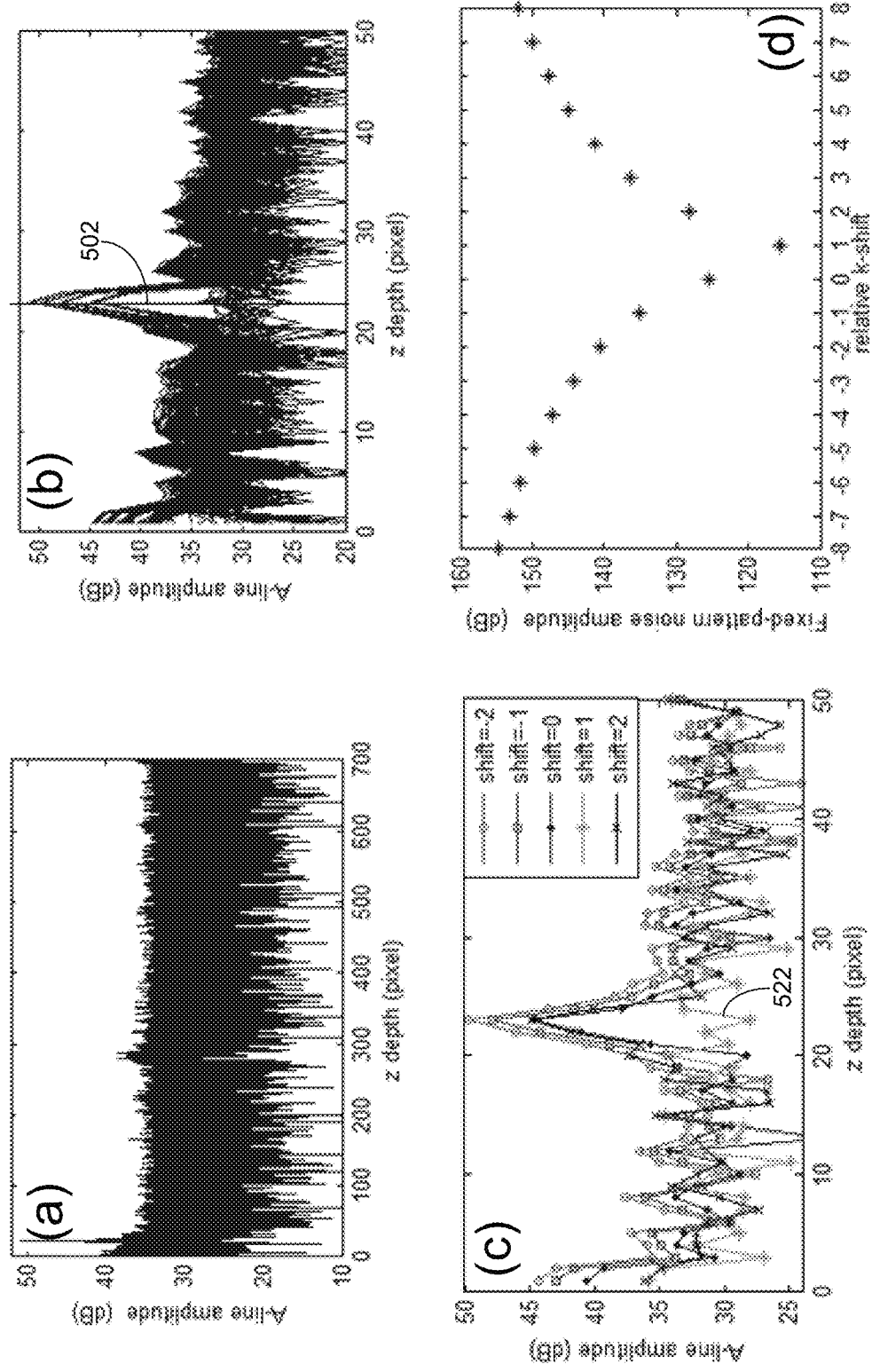
FIG. 5 shows example graphs illustrating an example calculation of a relative wavenumber shift between an SS-OCT spectral interferogram and a reference SS-OCT spectral interferogram in accordance with the disclosure.

To illustrate the search scheme of Method B described above, two hundred consecutive background interferograms were acquired by blocking the sample arm light. An arbitrary interferogram from the 200 interferograms was taken as the reference interferogram $A_r(n)$. This $A_r(n)$ was then subtracted from the remaining interferograms, and the differences were inverse Fourier transformed. The 200 A-lines after the inverse Fourier transform were plotted and shown in FIG. 5, panel a, and the first 50 pixels in depth are shown in FIG. 5, panel b. The vertical green line (line 502) in FIG. 5 panel b shows the location of the residual fixed-pattern noise. In this example, the depth location for the fixed-pattern noise corresponded to 0.0164N. The amplitudes at the residual fixed-pattern noise location were found to be divided into 5 groups, with the lowest signal group around the noise floor. According to FIG. 4 and Equation 4 above, the substantial amplitude difference at the residual fixed-pattern noise location was caused by the trigger jitter. The differences between the groups corresponded to different $m_s$ between the interferograms and reference interferogram $A_r(n)$.

In order to find the value of the relative wavenumber shift between an interferogram of interest and $A_r(n)$, relative wavenumber (k) shifts were introduced between the reference interferogram and the interferogram under evaluation. The A-line amplitudes at the residual fixed-pattern noise location were evaluated as shown in FIG. 5, panel c. In FIG. 5, panel c, the A-line under evaluation was reevaluated after subtracting the shifted interferograms by the reference interferogram. The residual fixed-pattern noise amplitude was obtained by summing the A-line amplitude over 3 pixels centered at its peak. This was then evaluated as a function of the k-shift. The relative trigger jitter in k-space was found as the k-shift at which the residual fixed-pattern noise was minimized as shown in FIG. 5, panel d. In FIG. 5, panel c the green line (line 522) with relative k-shift of 1 shows a minimum value at the location of residual fixed-pattern noise; i.e., the relative trigger jitter in k-space was found as the k-shift at which the fixed-pattern noise amplitude was minimized, +1 in this example. By repeating this procedure for the rest of the interferograms, all the collected interferograms can be aligned to the reference interferogram.

In order to compare the results of method A and method B described above, acquired interferograms from a human retina were aligned using both method A and method B. In some examples, after the alignment of all interferograms, the values for the first or last few wavenumber sample points in some interferograms may be missing. The missing values could be obtained by interpolation, simply adding zeros or using the adjacent data values. However, it was found that the best image quality was obtained when the first and last few wavenumber sample points were removed before performing further data processing. Then, typical Fourier domain OCT (FD-OCT) data processing procedures were applied. These include background (average of 200 aligned background interferograms) subtraction, Gaussian window spectral shaping, numerical dispersion compensation, and inverse Fourier transform.

Figure 6:
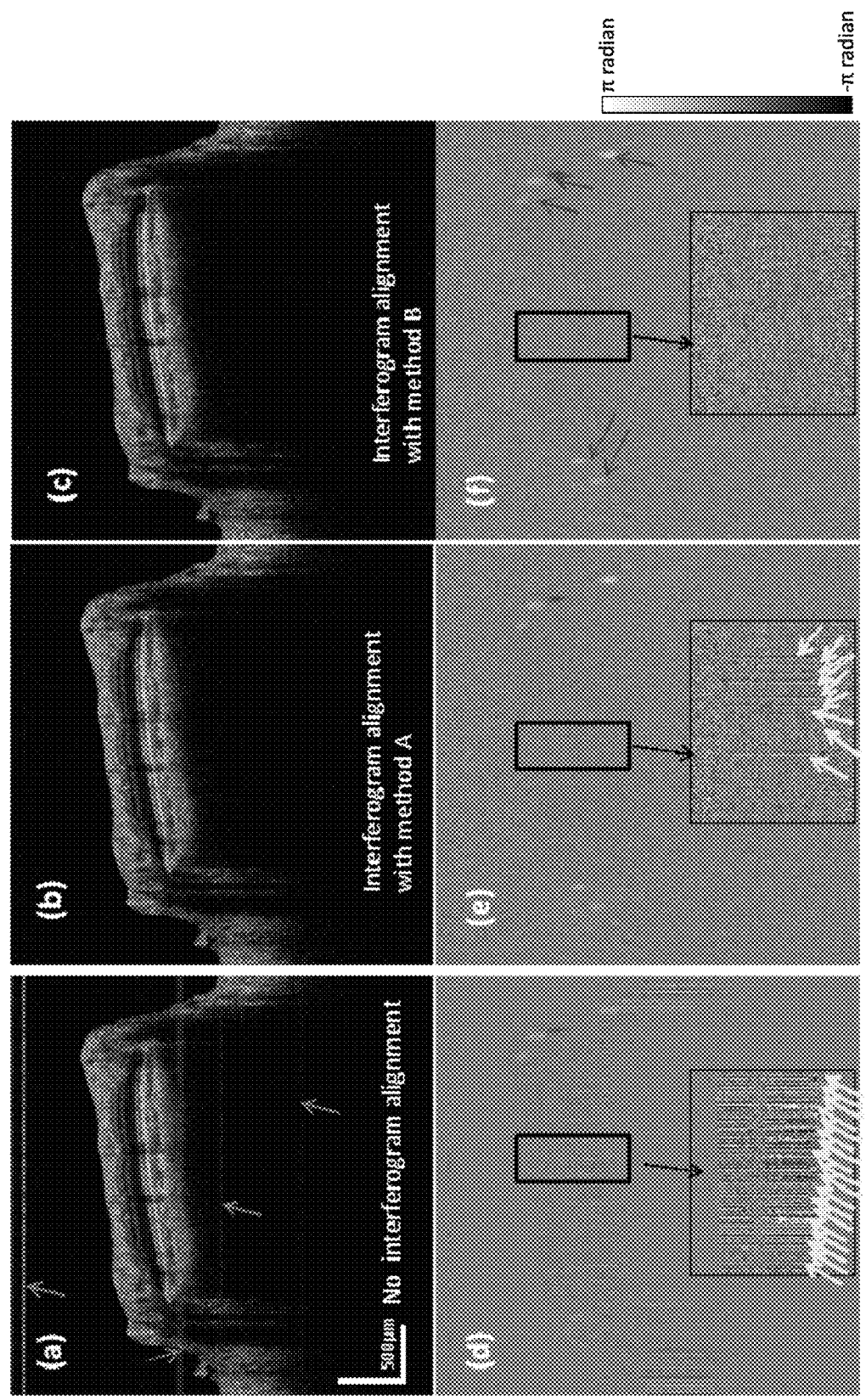
FIG. 6 shows example OCT images of a human retina generated without and with the herein-described spectral interferogram alignment.

The effect of fixed-pattern noise removal and phase stability improvement can be seen from the human retinal OCT intensity and Doppler images shown in FIG. 6. The images in FIG. 6 were generated from 3200 interferograms acquired by a circular scan pattern with diameter of 1.5 mm around the optic disk region. In particular, FIG. 6 shows OCT intensity (top row) and Doppler (bottom row) images of a normal human retina. The images contained 3200 interferograms acquired by a circular scan pattern with a diameter of 1.5 mm around the optic disk region in a healthy volunteer. Typical FD-OCT processing steps without interferogram alignment were used to obtain the image shown in FIG. 6, panel a. Firstly, the DC and lower frequency offset for each interferogram were removed by subtracting the mean of background interferograms. Then Gaussian-window spectral shaping, numerical dispersion compensation and inverse fast Fourier transform were applied. FIG. 6, panel a shows results from typical FD-OCT processing procedures without wavenumber alignment. In FIG. 6, panel a, the green arrows indicate the residual fixed-pattern noise. To get FIG. 6, panel b, all the interferograms were re-aligned using the above-described phase-based method A and FD-OCT processing steps were applied after that. In FIG. 6, panel c, all the interferograms were re-aligned using the above-described intensity-based method B and typical FD-OCT processing steps were applied after that. FIG. 6, panel d, panel e, and panel f are the corresponding Doppler OCT images for FIG. 6, panel a, panel b, and panel c, respectively. In FIG. 6 panel d, panel e and panel f, the region indicated by the small black rectangle was utilized for a performance evaluation. The insets indicated by the large black rectangle are the magnified images of the smaller rectangle and used for a phase stability evaluation. The yellow arrows indicate the locations that have residual phase errors induced by trigger jitter. More reduced residual phase errors were found in FIG. 6, panel e as compared to FIG. 6, panel d. Substantially no residual phase error was found in FIG. 6, panel f. The red arrows in FIG. 6, panel f show blood vessels.

After wavenumber alignment, the residual fixed-pattern noise artifacts, as indicated by green arrows in FIG. 6, panel a, were greatly reduced as shown in FIG. 6 panel b and panel c. Laser trigger jitter induced phase instability, which manifests as depth dependent phase difference as shown in FIG. 6, panel d, was greatly reduced as shown in FIG. 6 panel e and 6 panel f. As demonstrated in the insets of FIG. 6 panel e and panel f, it was found that method B gave better results than method A. In FIG. 6 panel f, substantially no residual phase error was found. However, method A required less processing time. For the alignment of 3200 interferograms, method A took 0.2496 seconds and method B took 20.4672 seconds using Matlab 2012a running on a laptop with an Intel Core i5-3340 CPU.

Total retinal blood flow of diabetic patient. In this example, the wavenumber alignment algorithm (intensity-based method B) was applied to a total retinal blood flow (TRBF) calculation with Doppler OCT. The TRBF was obtained using the en face technique described by Bauman et al. [7]. Multiple volumetric scans were obtained. In each volume, TRBF was calculated by integrating the Doppler shift in vessel areas on an optimized en face plane. Then, TRBF was averaged among volumes to reduce variation from cardiac pulsatility.

Previously, Baumann et al. proposed a numerical method to correct the trigger jitter induced phase instability [7]. The slope of the phase ramp was estimated based on the phase sampled at two different depths, and this slope was used to correct the trigger jitter induced phase instability. However, errors from the estimation of the phase ramp will affect all depths in the same A-scan. The propagation of errors might reduce the image quality of Doppler phase shift.

Figure 7:
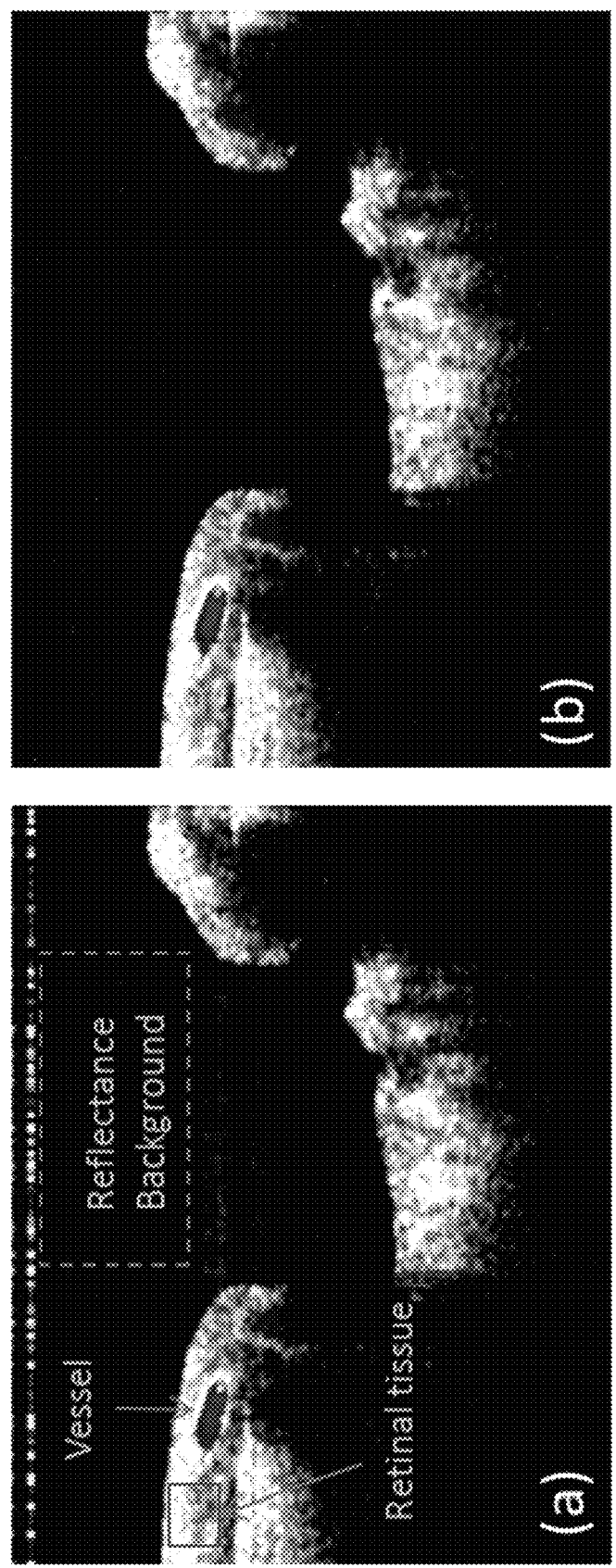
FIG. 7 shows an example Doppler OCT retinal image without and with the herein-described spectral interferogram alignment.

In this example, the signal-noise ratio (SNR) between the method proposed by Bauman et al. and the wavenumber alignment algorithm described herein were compared. This comparison is shown in FIG. 7. In particular, FIG. 7 shows Doppler OCT retinal images from a diabetic patient generated using an algorithm described in Bauman et al. in FIG. 7 panel a and the wavenumber alignment algorithm described herein in FIG. 7 panel b. These two methods were used to process the same raw data, and the TRBF calculation was the same, except for the trigger jitter/bulk motion correction. In this example, the volume scan covered a 1.6×2 $mm^2$ area of the optic disc and had 80 B-scans with 600 A-lines per B-scan. One cross section corresponding to a vertical line scan was selected to compare results between the methods. FIG. 7 panel a shows a cross section image obtained using Bauman's algorithm. Three regions were selected for signal-to-noise ratio (SNR) calculations. The SNR was defined as the ratio of average value in the signal region and the standard deviation of the signal in background area. In particular, the SNR of Doppler phase shift (SNR_D) was taken as the ratio of the average phase shift in a vessel and the standard deviation of the phase shift in static retinal tissue. The SNR of intensity (SNR_I) was taken as the ratio of the average intensity in retina tissue and standard deviation of intensity in background. In the image shown in FIG. 7, panel a, SNR_D=6.65 and SNR_I=27.86. FIG. 7, panel b, shows a cross section image obtained using the wavenumber alignment method described herein. In the image shown in FIG. 7, panel b, SNR_D=7.47 and SNR_I=43.45.

In this example, for the OCT intensity image, the signal region was taken as the retinal tissue region. For the Doppler OCT image, the signal region was taken as the retinal vessel, and the background was taken as the static retinal tissue where the Doppler shift should be zero. The SNR of Doppler phase shift is important in detecting vessels from the retinal tissue, for example. In FIG. 7, the alignment algorithm described herein had higher SNR for both the OCT intensity (43.45 vs 27.86) and Doppler OCT images (7.47 vs 6.65). The SNR of the OCT intensity image was increased because of less noise in the background (29.56 vs 74.48). The SNR of Doppler phase shift was increased because of the higher value of Doppler phase shift in the vessel area (average=1.51 vs 1.34, unit: rad). Thus, the approaches described herein increase image quality and thereby potentially enhance automatic detection of retinal tissue/vessels and increase the accuracy of TRBF measurements, for example.

Embodiments described herein use the information at the residual fixed-pattern noise location to align the acquired interferograms to remove or substantially reduce residual fixed-pattern noise artifacts and increase phase stability of the SS-OCT system. Generally, the approaches described herein may work within the imaging range for all SS-OCT systems with residual fixed-pattern noise. To achieve the best performance, the location of the reference residual fixed-pattern noise may be selected to be around the zero frequency or close to the maximum imaging range of the OCT system so that the sample image will not be overlapped with the reference residual fixed-pattern noise. However, if the OCT system does not have residual fixed-pattern noise and one still desires to improve the system phase stability, an artificial fixed-pattern noise artifact may be generated. As an example, this could be achieved by adding a thin glass plate in the reference arm or using a calibration mirror with an OCT signal that appears in the imaging range of the system [3, 5-7].

Figure 9:
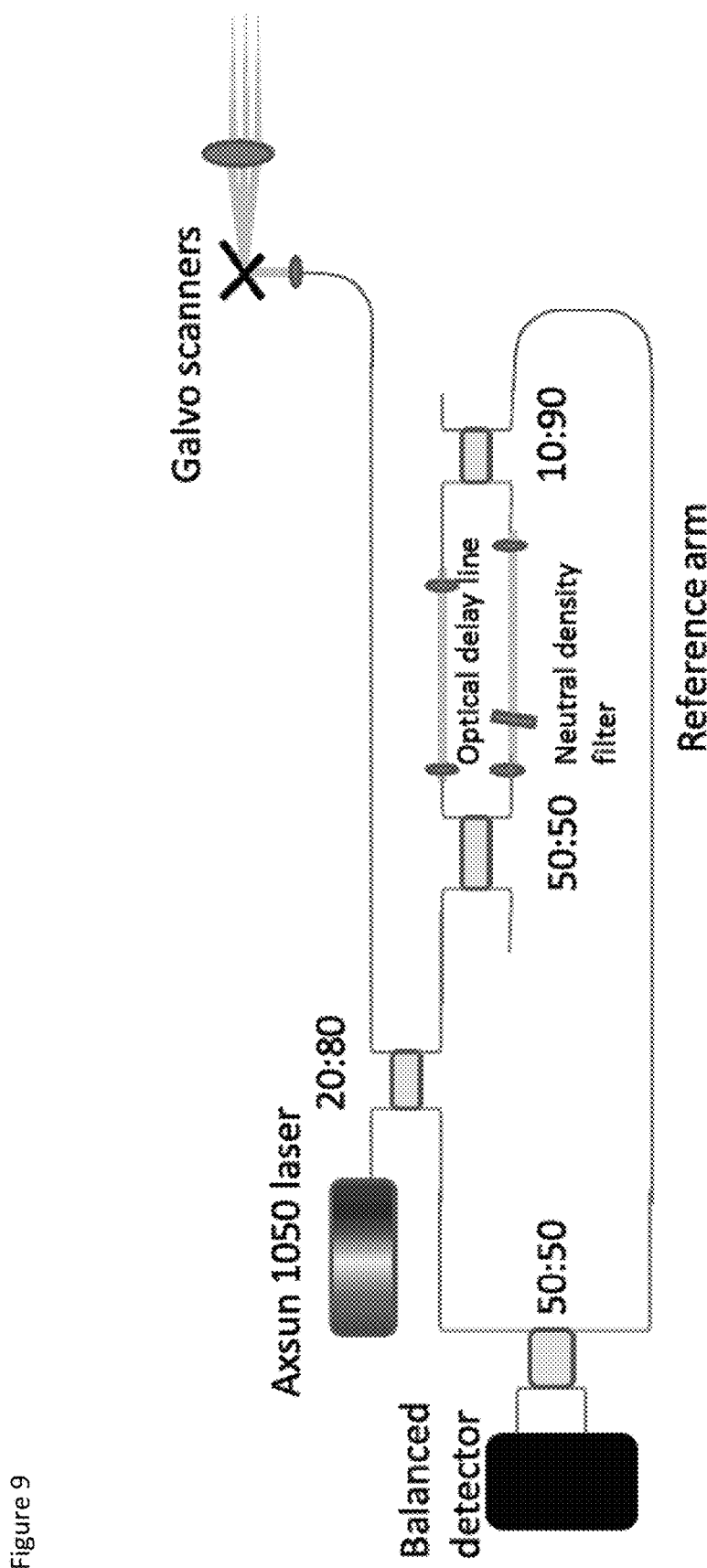
FIG. 9 schematically shows an example of an OCT system with double delay lines in the reference arm.
Figure 10:
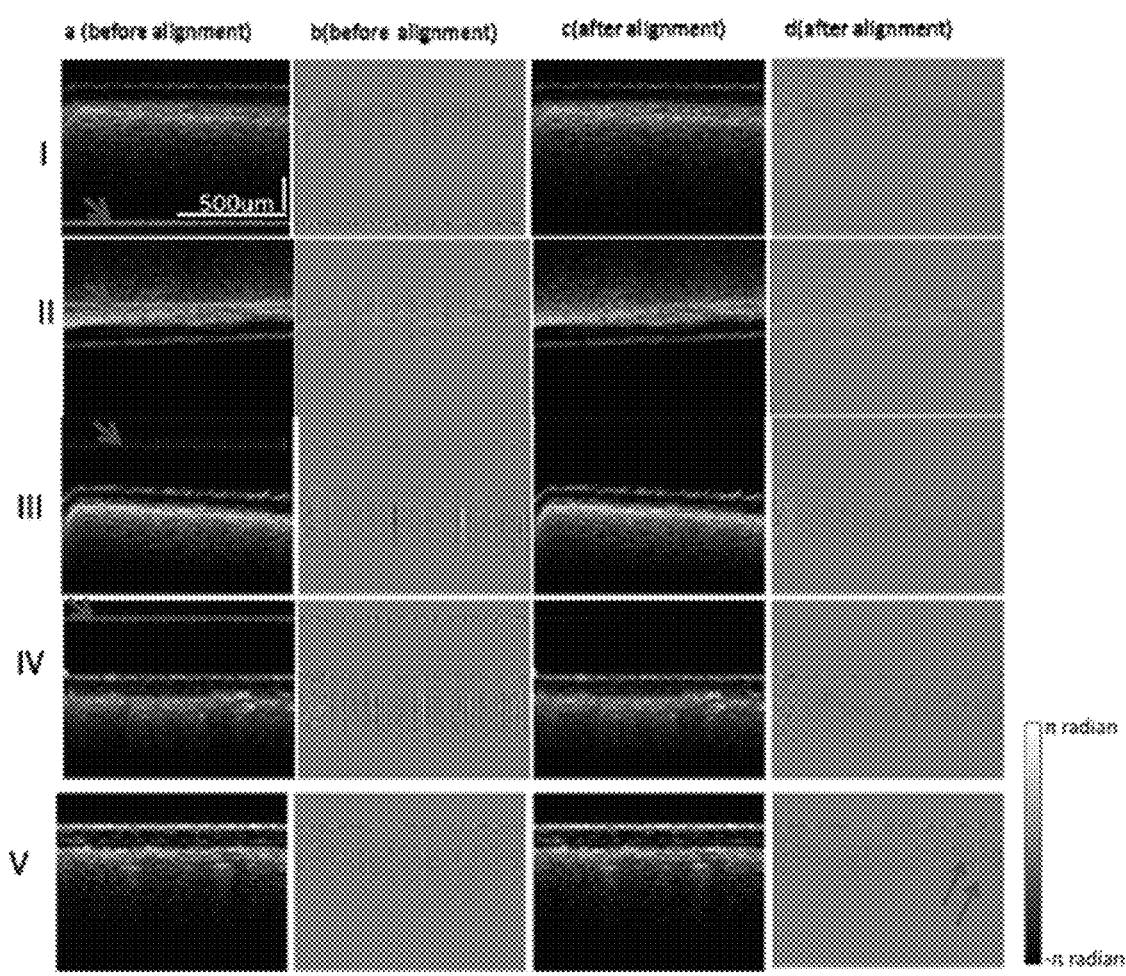
FIG. 10 shows examples of the minimization of fixed-pattern artifact and reduction of trigger jitter using the herein-described method B for different experimental conditions.

Embodiments of Method B described herein use intensity/amplitude values as the cost function to find the relative wavenumber shift between two A-lines. This approach is more robust than the method A and can be used to reduce trigger jitter and improve the system phase stabilities in various situations. As a demonstration, an OCT system (FIG. 9) with double delay lines in the reference arm was built. The two delay lines formed a Mach-Zehnder interferometer. One arm of the Mach-Zehnder interferometer was used to generate the fixed-pattern line in the image. The depth location of the fixed-pattern line can be tuned by changing the length of corresponding delay line. The same Axsun 1050 laser used in previous sections was used as light source. The signal from a balanced detector was sampled with a high speed digitizer (Alazar Technologies Inc., ATS 9350) using the built-in trigger and clock signals from the Axsun laser. FIG. 10 shows the results of trigger jitter reduction with method B. An infrared viewing card was used as the sample. All of the images contain 256 A-lines. In the FIG. 10, a few situations are demonstrated. Columns a and b of FIG. 10 show the structure and Doppler OCT images of a sample (an infrared sensor card) without interferogram alignment. Columns c and d of FIG. 10 show the structure and Doppler OCT images of the sample after interferogram alignment using method B. The red arrows show the location of fixed-pattern lines. The fixed-pattern lines are located close to the maximum imaging range of the system (row I), overlapped with sample image (row II), a result of 1st order coherence revival (row III), and a result of 2nd order coherence revival (row IV). The method B proposed here is able to successfully reduce the reduce trigger jitter and improve the system phase stabilities as demonstrated in columns c and d in FIG. 10. For the situation in row V of FIG. 10, there is no fixed-pattern noise (or line) in the images and the disclosed embodiment of method B is still able to reduce trigger jitter and improve the phase stability of the system. This is achieved by finding the relative wavenumber shift through minimizing the residual amplitudes of the sum of the first 20 pixels close to the zero delay. However, a few no residual phase errors are found as indicated by the blue arrows in FIG. 10 (row V column d).

Figure 11:
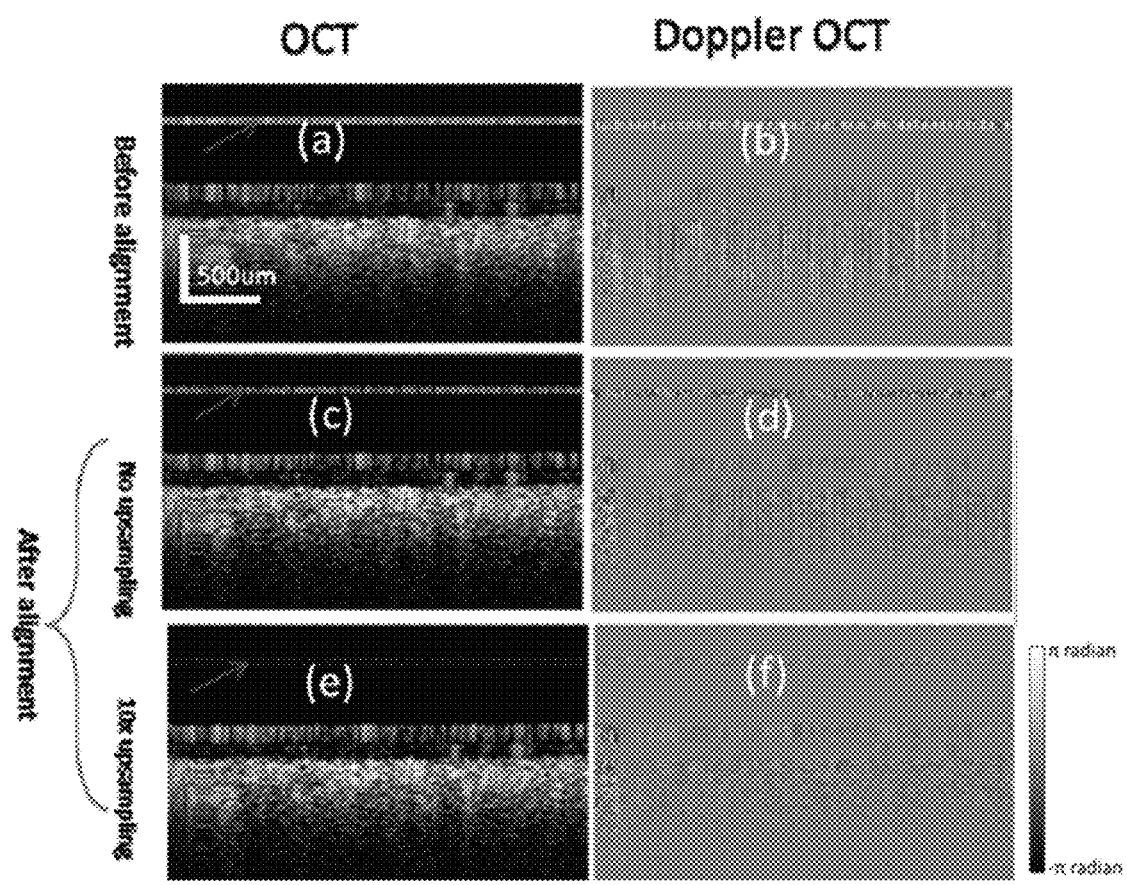
FIG. 11 shows examples of minimization of fixed-pattern artifact and reduction of trigger jitter using method B for a system with a constant sampling clock instead of an external optical k-clock.

Embodiments of methods described herein can also be used to reduce trigger jitter and improve the phase stability of SS-OCT systems that acquire the A-line interferograms with a constant sampling clock (either from the digitizer or from external constant clock) rather than an external optical k-clock. In such systems, the relative shift between two interferograms may not be an integer multiple of the sampling interval. A demonstration of the disclosed methods using a constant sampling clock system was performed using the setup shown previously in FIG. 9 where A-line interferograms were acquired with the constant sampling clock (125 MS/s) from the digitizer and the built-in A-line trigger from the laser. For this demonstration, 1120 data points were acquired in an A-line interferogram, and images were obtained by direct Fourier transformation of the interferograms without resampling to a linear k-space. A static infrared view card served as the sample. FIG. 11 shows an example of results obtained using the method B approach to process both OCT (panels a, c, and e) and Doppler OCT (panels b, d, and f) images from this system; images are shown obtained before (a and b) and after (c, d, e and f) interferogram alignment. The red arrows show location the fixed-pattern noise.

Using the approach described in the previous paragraph, it can be seen that the fixed-pattern line in FIG. 11, panel c is much weaker than that in FIG. 11 panel a, and phase noise in FIG. 11, panel d is weaker than that in FIG. 11, panel b. To fully stabilize the system phase with this setup, an up-sampling of the original A-line interferograms may be performed to allow for sub-point shift accuracy. FIGS. 11 panel e and 11 panel f show the results after applying method B to 10-fold up-sampled A-line interferograms, where an interpolation method based on frequency shifting and zero padding is used to up-sample the interferograms [10]. As shown in FIGS. 11 panel e and 11 panel f, application of the herein-disclosed methods using up-sampled data yields substantially improved results after alignment.

The scaling factor $\S(m_s, z)$ is the periodic function of $m_s \cdot z_f$. If $N/z_f$ is an integer, there are a number of $m_s$ that will make the scaling factor equal to zero. For example, if $N/z_f=5$, any $m_s=5 \cdot n$ will make the scaling factor zero. This may limit the maximum number of k-shifts that the method B can find. In an OCT system, the point spread function will usually take a few pixels instead of a single pixel and the fixed-pattern noise will usually take a few depth pixels in the image. So the correct relative k-shift can still be found by evaluating the sum of the A-line amplitude over a few pixels centered at $z_f$.

In some embodiments, the above described methods and processes may be tied to a computing system, including one or more computers. In particular, the methods and processes described herein, e.g., method 300 described above, may be implemented as a computer application, computer service, computer API, computer library, and/or other computer program product.

Figure 8:
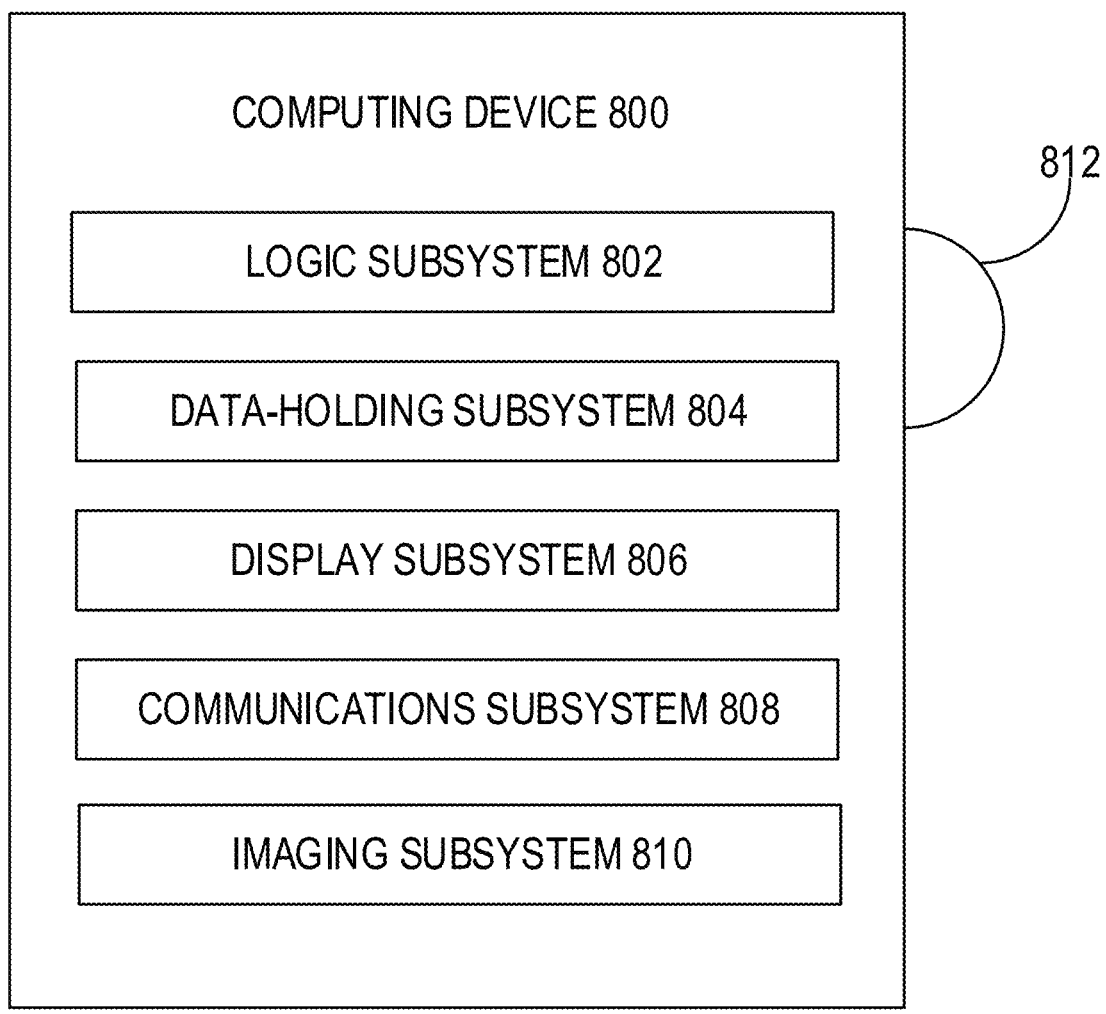
FIG. 8 schematically shows an example computing system in accordance with the disclosure.

FIG. 8 schematically shows a non-limiting computing device 800 that may perform one or more of the above described methods and processes. For example, computing device 800 may represent a processor included in system 100 described above, and may be operatively coupled to, in communication with, or included in an OCT system or OCT image acquisition apparatus. Computing device 800 is shown in simplified form. It is to be understood that virtually any computer architecture may be used without departing from the scope of this disclosure. In different embodiments, computing device 800 may take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 800 includes a logic subsystem 802 and a data-holding subsystem 804. Computing device 800 may optionally include a display subsystem 806, a communication subsystem 808, an imaging subsystem 810, and/or other components not shown in FIG. 8. Computing device 800 may also optionally include user input devices such as manually actuated buttons, switches, keyboards, mice, game controllers, cameras, microphones, and/or touch screens, for example.

Logic subsystem 802 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. For example, the one or more processors may comprise physical circuitry programmed to perform various acts described herein. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 804 may include one or more physical, non-transitory, devices configured to hold data and/or instructions executable by the logic subsystem to implement the herein described methods and processes. When such methods and processes are implemented, the state of data-holding subsystem 804 may be transformed (e.g., to hold different data).

Data-holding subsystem 804 may include removable media and/or built-in devices. Data-holding subsystem 804 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 804 may include devices with one or more of the following characteristics: volatile, nonvolatile, dynamic, static, read/write, read-only, random access, sequential access, location addressable, file addressable, and content addressable. In some embodiments, logic subsystem 802 and data-holding subsystem 804 may be integrated into one or more common devices, such as an application specific integrated circuit or a system on a chip.

FIG. 8 also shows an aspect of the data-holding subsystem in the form of removable computer-readable storage media 812, which may be used to store and/or transfer data and/or instructions executable to implement the herein described methods and processes. Removable computer-readable storage media 812 may take the form of CDs, DVDs, HD-DVDs, Blu-Ray Discs, EEPROMs, flash memory cards, USB storage devices, and/or floppy disks, among others.

When included, display subsystem 806 may be used to present a visual representation of data held by data-holding subsystem 804. As the herein described methods and processes change the data held by the data-holding subsystem, and thus transform the state of the data-holding subsystem, the state of display subsystem 806 may likewise be transformed to visually represent changes in the underlying data. Display subsystem 806 may include one or more display devices utilizing virtually any type of technology. Such display devices may be combined with logic subsystem 802 and/or data-holding subsystem 804 in a shared enclosure, or such display devices may be peripheral display devices.

When included, communication subsystem 808 may be configured to communicatively couple computing device 800 with one or more other computing devices. Communication subsystem 808 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 800 to send and/or receive messages to and/or from other devices via a network such as the Internet.

When included, imaging subsystem 810 may be used acquire and/or process any suitable image data from various sensors or imaging devices in communication with computing device 800. For example, imaging subsystem 810 may be configured to acquire OCT image data, e.g., interferograms, as part of an OCT system, e.g., OCT system 102 described above. Imaging subsystem 810 may be combined with logic subsystem 802 and/or data-holding subsystem 804 in a shared enclosure, or such imaging subsystems may comprise periphery imaging devices. Data received from the imaging subsystem may be held by data-holding subsystem 804 and/or removable computer-readable storage media 812, for example.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

REFERENCES

The following numbered references are cited throughout this disclosure by inclusion of the numbered references in square brackets. Each of the following references is hereby incorporated by reference in its entirety.
1. H. C. Hendargo, R. P. McNabb, A.-H. Dhalla, N. Shepherd, and J. A. Izatt, Biomed. Opt. Express 2 (2011) 2175.
2. T. Klein, W. Wieser, L. Reznicek, A. Neubauer, A. Kampik, and R. Huber, Biomedical Optics Express 4 (2013) 1890.
3. B. Vakoc, S. Yun, J. de Boer, G. Tearney, and B. Bouma, Opt Express 13 (2005) 5483.
4. Y.-J. Hong, S. Makita, F. Jaillon, M. J. Ju, E. J. Min, B. H. Lee, M. Itoh, M. Miura, and Y. Yasuno, Optics Express 20 (2012) 2740.
5. G. Liu, M. Rubinstein, A. Saidi, W. Qi, A. Foulad, B. Wong, and Z. Chen, Opt Express 19 (2011) 11880.
6. D. C. Adler, R. Huber, and J. G. Fujimoto, Opt Lett 32 (2007) 626.
7. B. Baumann, B. Potsaid, M. F. Kraus, J. J. Liu, D. Huang, J. Hornegger, A. E. Cable, J. S. Duker, and J. G. Fujimoto, Biomed Opt Express 2 (2011) 1539
8. B. Braaf, K. A. Vermeer, V. A. D. P. Sicam, E. v. Zeeburg, J. C. v. Meurs, and J. F. de Boer, Opt. Express 19 (2011) 20886.
9. W. Choi, B. Potsaid, V. Jayaraman, B. Baumann, I. Grulkowski, J. J. Liu, C. D. Lu, A. E. Cable, D. Huang, J. S. Duker, and J. G. Fujimoto, Opt Lett 38 (2013) 338
10. S. Yun, G. Tearney, J. de Boer, and B. Bouma, Opt Express 12 (2004) 4822.

The invention claimed is:

1. A computer-implemented method of aligning swept-source optical coherence tomography (SS-OCT) spectral interferograms, comprising:
calculating a relative wavenumber shift between an SS-OCT interferogram and a reference SS-OCT interferogram based on signal information of the SS-OCT interferogram and the reference SS-OCT interferogram at a fixed-pattern noise location, wherein the reference SS-OCT interferogram and the SS-OCT interferogram are obtained with a same interferometer;
aligning the SS-OCT interferogram to the reference SS-OCT interferogram based on the calculated relative wavenumber shift; and
generating an OCT image based on the aligned SS-OCT interferograms and outputting the generated OCT image to a display device.

2. The method of claim 1, further comprising:
for each SS-OCT interferogram in the SS-OCT interferograms:
calculating a relative wavenumber shift between the SS-OCT interferogram and the reference SS-OCT interferogram based on signal information of the SS-OCT interferogram and the reference SS-OCT interferogram at the fixed-pattern noise location; and
aligning the SS-OCT interferogram to the reference SS-OCT interferogram based on the calculated relative wavenumber shift.

3. The method of claim 1, wherein the signal information of the SS-OCT interferogram and the reference SS-OCT interferogram comprises amplitude or intensity information.

4. The method of claim 1, wherein the signal information of the SS-OCT interferogram and the reference SS-OCT interferogram comprises phase information.

5. The method of claim 1, wherein the signal information of the SS-OCT interferogram and the reference SS-OCT interferogram comprises both phase and amplitudeintensity information.

6. The method of claim 1, wherein aligning the SS-OCT interferogram to the reference SS-OCT interferogram based on the calculated relative wavenumber shift comprises multiplying an inverse Fourier transform of the reference SS-OCT interferogram by a scaling factor, wherein the scaling factor is calculated based on the calculated relative wavenumber shift.

7. The method of claim 6, wherein the scaling factor is calculated according to the following equation:

$$e^{-i\frac{2\pi}{N}m_s z} - 1$$

where $m_s$ is the relative wavenumber shift, N is the number of wavenumber samples in the SS-OCT interferogram, and z is a depth of the fixed-pattern noise location.

8. The method of claim 1, wherein calculating the relative wavenumber shift between the SS-OCT interferogram and the reference SS-OCT interferogram comprises calculating the relative wavenumber shift from the phases, amplitudes or complex values of $I_r(z_f)$, $I_s(z_f)$ and $I_{sr}(z_f)$, where $z_f$ is a depth of the residual fixed-pattern noise location $I_r(z_f)$ is an inverse Fourier transform of the reference SS-OCT interferogram at depth $z_f$, $I_s(z_f)$ is an inverse Fourier transform of the SS-OCT interferogram of interest at depth $z_f$, and $I_{sr}(z_f) = I_s(z_f) - I_r(z_f)$.

9. The method of claim 1, wherein calculating the relative wavenumber shift between the SS-OCT interferogram and the reference SS-OCT interferogram comprises introducing wavenumber shifts (k-shifts) in the SS-OCT interferogram and searching for a k-shift that minimizes an amplitude of the SS-OCT interferogram at the fixed pattern noise location, and wherein the relative wavenumber shift comprises a k-shift that minimizes the amplitude of the SS-OCT interferogram at the fixed pattern noise location.

10. The method of claim 9, wherein the amplitude of the SS-OCT interferogram at the fixed pattern noise location comprises a sum over a few pixels centered at a peak of fixed pattern noise at the fixed pattern noise location.

11. The method of claim 1, wherein calculating the relative wavenumber shift between the SS-OCT interferogram and the reference SS-OCT interferogram comprises calculating the relative wavenumber shift using only phase information at the residual fixed pattern noise location.

12. The method of claim 1, wherein the relative wavenumber shift ($m_s$) between the SS-OCT interferogram and the reference SS-OCT interferogram is calculated according to the following equation:

$$m_s = \text{angle}[I_s(z_f)/I_r(z_f)] * N/(2\pi z_f)$$

where $z_f$ is a depth of the residual fixed-pattern noise location, N is the number of wavenumber samples in the SS-OCT interferogram, $I_r(z_f)$ is an inverse Fourier transform of the reference SS-OCT interferogram at depth $z_f$, $I_s(z_f)$ is an inverse Fourier transform of the SS-OCT interferogram of interest at depth $z_f$, and angle[] is a phase extraction function.

13. The method of claim 1, further comprising removing the first and last one or more wavenumber sample points from the aligned SS-OCT interferograms.

14. The method of claim 1, further comprising performing background subtraction, Gaussian window spectral shaping, numerical dispersion compensation, and/or inverse Fourier transforms on each aligned SS-OCT interferogram.

15. The method of claim 1, wherein the fixed-pattern noise location is around a zero frequency or close to a maximum imaging range of an SS-OCT system used to acquire the SS-OCT interferograms.

16. The method of claim 1, further comprising introducing an artificial fixed-pattern noise artifact at the fixed-pattern noise location prior to aligning the SS-OCT interferogram and the reference SS-OCT interferogram.

17. The method of claim 1, wherein the reference SS-OCT interferogram comprises a single interferogram.

18. The method of claim 1, wherein the reference SS-OCT interferogram comprises a single background interferogram.

19. The method of claim 1, wherein the OCT image comprises a structural OCT image or a Doppler OCT image.

20. A system for aligning swept-source optical coherence tomography (SS-OCT) spectral interferograms, comprising:
   an SS-OCT system comprising a swept-source laser, the SS-OCT system configured to acquire SS-OCT interferograms;
   a logic subsystem; and
   a data holding subsystem comprising machine-readable instructions stored thereon that are executable by the logic subsystem to perform the steps of claim 1.

21. The system of claim 20, wherein the swept-source laser has a central wavelength of approximately 1050 nm.

* * * * *